United States Patent [19]

Stewart et al.

[11] Patent Number: 6,087,452

[45] Date of Patent: Jul. 11, 2000

[54] METAL-CHELATING SURFACTANT

[75] Inventors: Russell Stewart, Salt Lake City; Karin D. Caldwell, Salt Lake County; Chih-hu Ho, Sandy; Loren Limberis, Salt Lake County, all of Utah

[73] Assignee: University of Utah, Salt Lake City, Utah

[21] Appl. No.: 09/089,022

[22] Filed: Jun. 2, 1998

[51] Int. Cl.[7] .............................. C08F 293/00; C08L 3/04; C08L 53/00; C07K 1/00; C07K 14/00

[52] U.S. Cl. ............................ 525/323; 525/299; 525/90; 523/1; 523/407; 524/68; 436/56; 436/73; 530/402

[58] Field of Search ...................................... 436/532, 531, 436/823, 533, 56, 86; 530/391.1, 816, 387, 402; 435/181; 525/323, 299, 90; 524/68; 523/1, 407

[56] References Cited

U.S. PATENT DOCUMENTS 5,516,703  5/1996  Caldwell .................................. 436/532
5,674,677  10/1997  Peterson .

*Primary Examiner*—Avis M. Davenport
*Attorney, Agent, or Firm*—James Sonntag

[57] ABSTRACT

A modified surfactant of the PLURONIC™-type compound and method for manufacture is disclosed. The surfactant compound has at least one PEO block attached at a first end to at least one PPO block, with at least one of the PEO block having an organic metal-chelating end group (R) attached to a second end, the remaining PEO blocks having an unmodified hydroxyl group at the second end. The metal-chelating group is charged with an metal-ion. A protein with a metal-affinity tag, e.g., a histidine tag, is then complexed with the metal-chelating group to form a complex of the modified surfactant, the metal ion, and the protein. The modified surfactant may be adsorbed upon a hydrophobic surface, charged with a metal ion, and then complexed with a protein with a metal-affinity tag. A surface with specific activity toward proteins is the presented, which is suitable for applications where a protein is immobilized upon a surface to give the surface specific protein activity.

32 Claims, 9 Drawing Sheets

Fig. 1

(His)₆
chelating group
Pluronic F108
protein
beads
(PEO)₁₂₉
(PPO)₅₆

Fig. 8

METAL-CHELATING SURFACANT

STATEMENT REGARDING FEDERALLY SPONSORED RESEARCH OR DEVELOPMENT

This invention was made with United States Government support under Grant No. CTS-9624907 by the National Science Foundation. The government may have certain rights in this invention.

FIELD OF THE INVENTION

This invention relates to the binding of proteins to PPO, PEO block copolymer surfactant molecules.

BACKGROUND OF THE INVENTION

The immobilization of active proteins at interfaces is a challenge common to many areas of applied biological technology. For example, immobilization of proteins at interfaces is required for diagnostic systems, such as immuno assays. In addition, proteins are attached to bio-compatible polymer for delivery into biological systems for diagnostic and therapeutic applications. Immobilization of proteins upon an interface is also required for the continuing development of ultra-sensitive instrumentation based on optical tweezers and scanned tip microscopes for probing the activities and mechanical properties of single protein molecules.

Any attachment of a protein for immobilization would ideally minimize structural perturbation and maximize protein activity, allow immobilization of proteins with a controlled orientation to the surface, and provide a consistent linkage compliance to the surface. This is important for accurate and consistent results when measuring the properties of a particular protein. Other properties of an ideal immobilization scheme are preservation of biomolecule activity, specificity, high binding stability, reversible binding under non-denaturing conditions, controlled immobilization density, and convenient co-immobilization of multiple proteins, or other molecules. Likewise, in complexes of a protein and a biomolecule that are not necessarily used in coatings, perturbation of the structure of the protein should be minimized, and the maximum protein activity be preserved.

Several approaches using chelated metal ions have been reported that allow histidine-tagged proteins to be immobilized at several types of interfaces, such as lipid interfaces and lipid monolayers with metal-chelating lipids, gold surfaces with self-assembling monolayers formed with metal-chelating alkanethiols, and oxide surfaces with metal-chelating silanes. A problem with these methods is that they are complex and not convenient to use.

U.S. Pat. No. 5,674,677 to Peterson describes a method for joining two amino acid sequences by coupling an organic chelator to an protein, e.g., an enzyme, and charging the chelator with a metal ion. This complex is then mixed with any protein containing a histidine tag to couple the complex with the histidine tagged protein.

So-called PLURONIC™ surfactants shall be referred to herein as 'P-surfactants'. P surfactants are poly(propylene oxide) (PPO) and poly(ethylene oxide) (PEO) block copolymers, and have been shown to be very passive with respect to protein activity. Certain P-surfactants have little or no affinity for proteins and form self-organized coatings on hydrophobic surfaces to provide a passive, non-active surface with respect to proteins. U.S. Pat. No. 5,516,703, to Caldwell et al. (Caldwell et al.), which is hereby incorporated by reference, describes a method for introducing reactive end groups to a P-surfactant, and chemically coupling to proteins through chemical covalent bonds with the reactive end group. The P-surfactant with the reactive end groups is adsorbed upon a surface, and then reacted to couple to a protein to immobilize the protein upon the surface.

The Caldwell et al. system is a successful method for immobilizing a protein on a surface that preserves the activity of the protein, and that prevents non-specific adsorption of proteins. However, the Caldwell et al. system has several limitations. Attachment to the P-surfactant must be through chemical reaction to form a covalent bond, and certain proteins do not lend themselves well to such attachment. For example, a preferred attachment in Caldwell et al. is through disulfide groups, which attach to thiol groups in amino acids. A particular protein may not have thiol groups, or the thiol groups may not be present in a suitable position in the protein for attachment. In addition, thiol groups may exist at multiple places in the protein, which allows attachment to the P-surfactant molecule at anyone or more of several locations. The result can distort the natural conformation of the protein, which can adversely affect its activity. In addition, the protein may not attach consistently and predictably where several thiol groups may be present.

OBJECTS OF THE INVENTION

It is, therefore, an object of the invention to provide a composition and method for attaching proteins to interfaces that is specific, has high binding stability, and has reversible binding under non-denaturing conditions.

It is another object of the invention to provide a composition and method for attaching to proteins that allows preservation of the biological activity of the attached bio-molecule.

It is another object of the invention to provide an immobilization of biomolecules upon a surface that allows a controlled immobilization density and allows convenient co-immobilization of multiple proteins or other molecules.

It is another object of the invention to provide a composition and method for binding a bio-molecule to a P-surfactant molecule.

It is another object of the invention to provide an immobilization method that provides a convenient and general method of protein immobilization that takes advantage of the self-organizing and protein-repelling properties of P-surfactants at hydrophobic interfaces.

It is another object of the invention to use a P-surfactant bio-compatible surfactant for specific attachment to a histidine-tagged proteins.

It is another object of the invention to use the activity preserving P-surfactant interface as a foundation for the specific immobilization of proteins tagged with a metal-affinity group through their affinity for metal ions chelated to a modified P-surfactant.

It is another object of the invention to provide an immobilization method that will be chemically robust and broadly applicable to most recombinant proteins, many non-recombinant proteins, and cells expressing recombinant proteins on their surface.

It is another object of the invention to provide for the immobilization of antibodies in immunodiagnostic reagents, immobilization of enzymes in biosensors, surface immobilization to study protein-ligand interactions, and immobilization of cells in bioreactors.

Further objects of the invention will become evident in the description below.

BRIEF SUMMARY OF THE INVENTION

The present invention is a composition and method, wherein a P-surfactant is modified with organic metal-chelating groups on the terminal ends of the PEO blocks. The metal chelating end groups, when charged with a suitable metal ion, can then be used for coupling to a protein with an amino acid sequence having affinity for metal ions.

The metal-chelating P-surfactant can be adsorbed upon a suitable hydrophobic surface. The metal-chelating P-surfactant is then charged with a metal ion, and a protein with metal-ion affinity may then be immobilized upon the surface. The resulting surface has specific protein activity and is essentially absent of non-specific activity.

P-surfactants are block copolymers having a hydrophobic center block with hydrophilic end blocks. The hydrophobic center block is poly(propylene oxide) (PPO) and the hydrophilic end blocks are poly(ethylene oxide) (PEO). P-surfactants are known as being non-immunogenic, and for their low activity toward proteins and low toxicity. When coated upon a hydrophobic surface, such as polystyrene, the center blocks are adsorbed onto a hydrophobic interface and self organize into a monolayer with the end blocks extending from the surface and waving freely in a seaweed-like fashion. The coverage of the hydrophobic center blocks and the action of the end blocks effectively blocks nonspecific adsorption sites on the substrate and creates a nonadsorbing surface to proteins, since the extending end blocks form a protein-repelling layer that prevents protein interaction and denaturation on the surface of the surface. Polymer surfactants of this type are also available under the name POLOXAMER$\phi$.

The metal-chelating P-surfactants of the invention are suitable for immobilizing proteins with metal affinity at interfaces, such as at solid/liquid interfaces, and at liquid/liquid interfaces. These include, for example, systems with micelles, gels and emulsions of the metal-chelating P-surfactant of the invention, or these containing the metal-chelating P-surfactant of the invention. Since P-surfactants are bio-compatible, having little immunogenic activity, and low toxicity, the metal-chelating P-surfactants of the invention may be used for applications such as drug delivery.

In a preferred embodiment of the present invention, recombinant, histidine-tagged proteins are immobilized at hydrophobic interfaces. The terminal hydroxyl groups of a P-surfactant are reacted to form a derivative with metal-chelating groups, such as nitrilotriacetic acid (NTA), at free ends of the hydrophilic PEO blocks. Metal ions chelated by the NTA group have coordination sites free to bond with electron donating or metal-affinity side-chains, particularly histidine residues, on the protein surface. Proteins can be given high affinity for chelated metal ions by genetically adding the electron donating side chains, such as terminal histidine residues. Through genetic engineering, any recombinant protein can be given high affinity for immobilized metal ions by genetically adding the proper tags of an electron donating amino acid sequence, such as consecutive histidine residues, to either end of the protein. Non-recombinant proteins can be chemically outfitted with histidine tags, or other suitable protein sequences, or other chelating sequences. Immobilization of these tagged proteins through their affinity for immobilized metal ions has several merits. Histidine tags in particular are small (usually only six amino acids) and therefore structurally and functionally benign. In addition, histidine tags and other tags can be added to either the amino- or carboxyl-terminus of recombinant proteins, which allows some control of the point of attachment to the P-surfactant. This allows a consistent orientation of the protein with the chelated P-surfactant and its immobilization orientation upon a surface.

The interaction between histidines and chelated ions, such as $Ni^{2+}$, has a high binding stability. The equilibrium dissociation constant ($K_d$) can be as low as $10^{-13}$ M. In addition, the interaction is reversible. However, immobilized proteins can be eluted relatively easily by lowering the pH, or eluted with a chelator that competes with the histidine tags for the $Ni^{2+}$ ion, such as a histidine analog, e.g. imidazole, or free chelators.

The present invention allows for high specificity towards metal-affinity tagged proteins, since the non-specific surface of the hydrophobic substrate is guarded by the P-surfactant molecule and is not available for further non-specific reaction or adsorption. Therefore, the only reactive sites available for protein binding are the terminal chelated metal groups on the P-surfactant. In addition, since the position of the histidine tags is controllable for many proteins and may be placed at either end of the protein, the attachment of the protein to the P-surfactant and a surface is more predictable. Conformation effects are minimized and the protein is less likely to be denatured by the attachment.

The reactive density of the composition of the invention can be easily controlled. This may be desirable to predetermine the density of reactive sites of a surface upon which a metal chelating P-surfactant/protein complex is adsorbed. Density can be controlled by mixing modified P-surfactant with unmodified P-surfactant. P-surfactant in its unmodified it essentially unreactive to any protein interaction, and when adsorbed upon a hydrophobic surface, the surface is essentially unreactive to any protein interaction. When modified P-surfactant is diluted with unmodified P-surfactant the activity is proportionally reduced, and when the mixture is adsorbed upon a hydrophobic surface, the reaction density upon the surface is likewise proportionally reduced. In this manner the density of immobilized proteins upon the surface can be controlled.

Co-reaction with more than one protein may be accomplished by having two or more different proteins, each with metal-affinity tags, bound to a metal chelating P-surfactant of the invention. This can be accomplished by exposing the metal chelating P-surfactant to a mixture of the proteins.

Accordingly, an aspect of the present invention is a modified P-surfactant having metal-chelating end groups. The end group when charged with a suitable metal ion forms a binding site to a metal-affinity tag on a protein amino acid sequence.

Another aspect of the present invention is a method for immobilizing a protein upon a hydrophobic surface comprising:

(1) adsorbing the modified P-surfactant having metal-chelating end groups upon a hydrophobic surface to form a layer of the modified P-surfactant on the surface;

(2) charging the modified P-surfactant coating by contacting the coating surface with an aqueous solution containing a suitable metal ion to form a chelated metal-ion complex of the metal-ion and the modified P-surfactant coating adsorbed upon the hydrophobic surface;

(3) contacting the charged coating with an aqueous solution containing a protein having a protein-affinity tag to link the histidine tag with the chelated metal ion.

Another aspect of the invention is a coated article having a hydrophobic surface with an adsorbed coating of metal-chelating P-surfactant, a chelated metal-ion, and a metal-affinity tagged protein linked to the metal ion.

The term 'PLURONIC™-type surfactant or P-surfactant', as used in this application, is any one of the class of compounds characterized as having at least one pendent hydrophilic block (PEO) with one end attached directly or by bridging structures to a hydrophobic block (PPO) and the other end attached to pendent —O—H groups. Preferably, the number of pendent hydrophilic blocks in the compound with attached —O—H groups (PEO—O—H) is between 1 and 6, and the number of PPO blocks is between 1 and 3. The length of the PPO blocks and PEO blocks may be any suitable length compatible with the intended use of the metal chelated P-surfactant. If the metal chelated P-surfactant is to be adsorbed upon a hydrophobic surface to, for example, immobilize a metal-affinity tagged protein thereon, the PPO blocks should be long enough to sufficiently adhere to the surface and the PEO block sufficiently long to shield the non-specific sites on the substrate. It is believed that for adsorption upon a surface, the PEO is —$(C_2H_4—O)_u$—, wherein the length or u is the same or different in each PEO block and is greater than 50. PPO is —$(—C_3H_6)_v$— wherein v is greater than 25. The bridging structures may be —$C_2H_4$—, —$C_3H_6$—, and >$NCH_2CH_2N$<. Preferred P-surfactants can be represented by the formula;

where y is between 25 and 75, preferably between 30 and 60, and x and z are preferably the same, but may be different, and are between 50 and 150, preferably 80 and 130.

If the metal-chelating P-surfactant is to be used to form a gel, micelle, emulsion, or the like for introduction into a biological system, the lengths of the PPO and PEO blocks are suitable for forming the gel or micelle, and include, but are not limited to, those defined above.

At least a portion of the pendent —O—H groups on the ends of the PEO groups are reacted to form a modified surfactant having —O—R groups in place of —O—H groups, where R is metal-chelating group. The metal-chelating end group may be any organic chelating groups that can be suitably attached to the terminal end of the PEO block of a P-surfactant by substituting the terminal —OH group with the chelating groups. Suitable metal-chelating end groups include, but are not limited to, nitrilotriacetic acid (NTA), iminodiacetic acid (IDA), bicinchoninic acid (BCA), or N,N,N'-tris(carboxymethyl)ethylenediamine (TED). The method for forming the metal-chelating group R may be any of the suitable chemistries for attaching chemical groups to the pendent ends of poly(ethylene oxide) compounds.

The metal ion is one compatible with the R chelating group, and one that has enough coordination sites to be chelated and also to bind to a metal-affinity tag on a protein sequence. These particularly include ions of the transition metals, lanthanides, and actinides, such as $Ni^{2+}$, $Cu^{2+}$, $Zn^{2+}$, and ions of gadolinium (Gd).

The protein has a metal-affinity tag. The metal-affinity tag is a chelating group with sufficient metal affinity to bind to the complex of the chelated metal ion and chelating groups at the end of the PEO blocks. The metal-affinity tag may be any suitable chelating group, but is preferably a sequence of adjacent amino acids that together function as a chelating group. A suitable metal-affinity tag is a histidine tag, which is a sequence of three or more adjacent histidines (usually six), which are usually on the carboxy or amino terminus end of the protein or amino acid sequence, but may be any accessible sequence of histidines in the protein or amino acid sequence. Some proteins have a natural affinity for metal-ions, but usually a metal-affinity tag is added to the protein by known recombinant or protein cloning methods. Other suitable protein sequences that contain amino acids with a metal-ion affinity may be used, and may contain the amino acids with a metal-ion affinity in a sequence or separated in a sequence by other amino acids. The metal-affinity tag should provide a sufficient number of amino acids with affinity for metal-ions in sufficient proximity to complex with the metal ion bound to the chelating group (R).

The surfaces upon which the metal-chelating P-surfactant can be adsorbed are hydrophobic surfaces. The hydrophobic surface is any suitable hydrophobic surface, preferably a polymeric substrate that is hydrophobic. Usually surfaces with a water contact angle greater than about 60°, preferably about 70°, are suitable. Suitable polymeric hydrophobic substances are polystyrene, polymethylmethacrylate, poly-olefins (polyethylene, polypropylene) polyvinylchloride, silicones, and block copolymers containing these constituents. The less hydrophobic polymer substrates (water contact angle between 60° and 70°), such as PVAc are also contemplated by the invention but are less preferred. Adsorption upon these polymers would be expected to be less than for more hydrophobic polymers such as PS and PMMA, and slow release of the surfactant from the polymer surface over time would be expected. Hydrophilic substrates such as silica, agarose, and polyvinyl alcohol are not contemplated by the present invention. However, it is contemplated that hydrophilic substrates may be treated to render them hydrophobic before adsorption thereon of the modified polymeric surfactant. For example, silica can be treated with dimethyl-dichloro silane to provide a hydrophobic surface.

The hydrophobic polymer may be porous or non-porous, be formed as a flat surface (e.g., a microtiter plate), microbeads, or the like. It may also be in the form of colloidal or latex particles. Examples of suitable substrates include, but are no limited to, microtiter plates, for use in immuno-assays, microbeads for chromatography, monodis-perse beads for immobilizing a protein for study, such as for use in optical tweezer applications. In addition, implants coated with metal chelating P-surfactant can be introduced with surfaces of immobilized cell attachment proteins having specific biological activity for attachment to cells in the body, and with no or little undesired non-specific activity that may induce an immune response.

DETAILED DESCRIPTION OF THE INVENTION

SUMMARY OF EXPERIMENTAL PROCEDURE

Using histidine-tagged firefly luciferase as a test protein, linking to a metal-chelating P-surfactants was done to provide an effective and convenient method for specifically immobilizing proteins with little loss of activity on polystyrene beads.

Preparation of Chelating Surfactant

P-surfactant F108 was used as the foundation. F108 is a triblock, having the formula as in (1) where y is 56 and x is 129. About 80 wt. % of F108 is PEO. The terminal hydroxyl groups of F108 are activated with p-nitrophenylchloroformate, then conjugated through a primary amine with nitrilotriacetic acid (NTA), synthesized separately from ε-amino-blocked lysine. (See Hochuli, E., Dobeli, H., and Schacher, A. (1987) "New metal chelate adsorbent selective for proteins and peptides containing neighboring histidine residues". *Journal of Chromat.* 411:177–184.) The resulting P-surfactant has three pendent carboxylic acid groups at the pendent ends of its PEO blocks that will form four coordination bonds with metal ions, leaving two coordination sites available to interact with histidine side chains.

Figure 1:
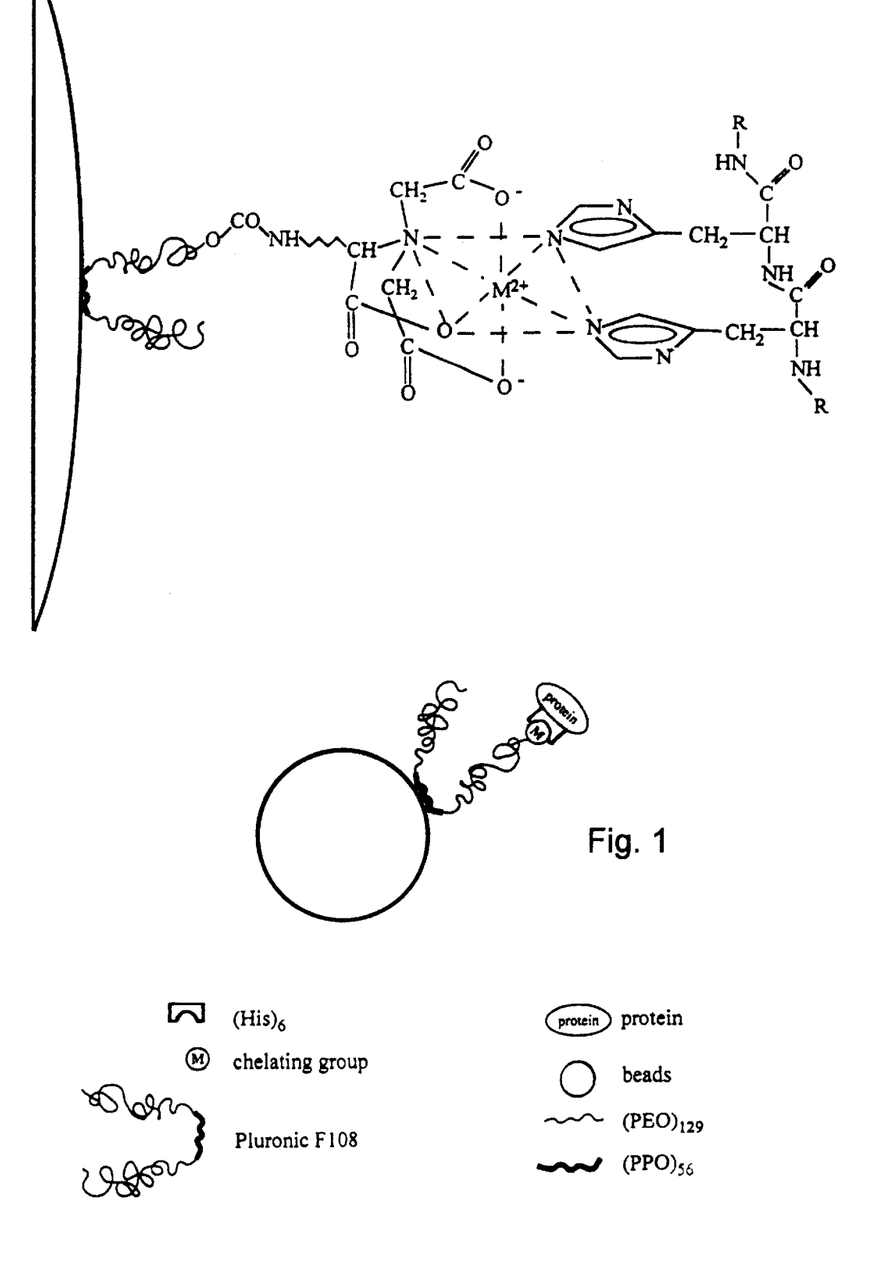
FIG. 1 is a schematic representation of histidine-tagged proteins immobilized on a hydrophobic surface.

With reference to FIG. 1 is shown an immobilization histidine-tagged proteins using NTA-derivatized P-surfactant F108. The hydrophobic PPO block of the P-surfactant F108 triblock copolymer interacts and adsorbs upon the hydrophobic surface of a polymer shape, such as polystyrene microspheres or beads. The hydrophilic NTA-modified PEO blocks extend into solution, creating an activity-preserving interface to which histidine-tagged proteins bind through chelated metal ions. The NTA complex has three pendent carboxylic groups forming four coordination bonds with a metal ion ($M^{2+}$). The metal ion has coordination sites free to bond with electron donating side chains of histidine residues.

EXAMPLES

Histidine-tagged recombinant firefly luciferase was used to evaluate protein immobilization on chelating P-surfactant F108. Firefly luciferase is a good model protein for several reasons: it is readily available, it is difficult to immobilize by conventional methods, its activity (generation of light from ATP) is convenient to assay, and there is considerable interest in using immobilized luciferase in biosensors. The examples will show that F108 prevents adsorption and denaturation of luciferase on hydrophobic beads, and allows specific and reversible immobilization of active firefly luciferase.

In this Example below the following experimental procedures were used.

Materials

N'-benzyloxycarbonyl-L-lysine, bromacetic acid, and p-nitrophenyl chloroformate were obtained from Sigma Chemicals Company (St. Louis, Mo.). Palladium on activated charcoal (Pd/C, 10% Pd contained) was obtained from Aldrich Chemical Company (Milwaukee, Wis.). P-surfactant F108 was obtained from BASF Corp. (Mount Olive, N.J.). Benzene, NaOH, $Na_2SO_4$ anhydrous, HCl and ether were obtained from Fisher Scientific (Pittsburgh, Pa.).

Polystyrene (PS) beads with the diameter of 0.453 μm were purchased from Seradyn Particles Inc. (Indianapolis, Ind.).

Synthesis of $N^\alpha,N^\alpha$-bis (carboxymethyl)-L-lysine (ε-amino-NTA)

Bromacetic acid (28 g, 200 mmole) was dissolved in 100 ml of 2 M sodium hydroxide (NaOH) and cooled to 0° C. A solution of 28 g (100 mmole) of N'-benzyloxycarbonyl-L-lysine in 150 ml of 2 M NaOH was slowly added dropwise into the bromacetic acid solution while stirring in a 0° C. cooling bath. After 2 hours, the cooling bath was removed and the solution was stirred overnight at room temperature. The solution was then heated for two hours at 50° C. and 300 ml of 1 M hydrochloric acid (HCl) was added dropwise. The mixture was then cooled to room temperature allowing the N'-benzyloxycarbonyl-nitrilotriacetic acid (Z-NTA) to precipitate. The Z-NTA was collected by filtration and further purified by dissolving in 1 M NaOH, re-precipitating with the same amount of 1 M HCl and filtering. The dissolving and precipitating cycle was repeated twice.

The Z-NTA was hydrogenated to remove the protecting group (Z) from the ε-amino group. The Z-NTA (15 g, 37.5 mmole) was dissolved in 300 ml of methanol. A spatula tip of 10% Pd/C was added to the solution and $H_2$ gas was bubbled into the solution at room temperature and normal pressure for 3 hours. The solvent was removed by evaporation and the remaining product was dissolved in 50 ml D.I. water. The solid Pd/C was removed from the NTA by filtration. The ε-amino NTA solution was then added to 1000 ml ethanol at 0° C. A white precipitate of ε-amino-NTA formed within 2 days.

Activation of P-surfactant F108 with p-nitrophenyl Chloroformate

P-surfactant F108 (6 g, 0.4 mmole) was dissolved in 18 ml benzene and added dropwise into a stirred solution of p-nitrophenyl chloroformate (0.5 g, 1.2 mmole) in 18 ml benzene. The reaction was continuously stirred at room temperature for 24 hours. This solution was then slowly added into a beaker which contained approximately 600 ml ether (15 reaction solution volumes) to precipitate the activated F108-nitrophenyl product (F108-ONP). The ether was continuously stirred during the precipitation reaction to increase the yield. The precipitate was collected by vacuum filtration and flintier purified by two additional cycles of dissolving in benzene and precipitating in ether. The F108-ONP product was stored in a vacuum desiccator containing $CaCl_2$ to prevent hydrolysis of the ONP group.

Synthesis of F108-NTA

The ε-amino-NTA was dissolved in D.I. water and the pH was adjusted to 6.0 with 2 N NaOH. The sodium salt of ε-amino-NTA was then precipitated in ethanol. F108-ONP (3.5 g, 0.233 mmole) in 30 ml of anhydrous methanol was slowly added to the sodium salt of δ-amino-NTA (3.5 g, 10.57 mmole) in 270 ml of anhydrous methanol. The molar ratio of F108-ONP to NTA was approximately 1:45. The solution was mixed at room temperature and the reaction of F108-ONP with ε-amino-NTA was monitored by the shift in the maximum peak of 268 nm to 310 nm as ONP was released. When the reaction was complete, after 72 hours, the solution was concentrated by evaporation. The concentrated solution (25% of the original volume) was precipitated in ether to remove the free ONP. The precipitated F108-NTA was dissolved in water and dialyzed against water for two days to remove free NTA and ONP. The F108-NTA solution was freeze dried and stored in a desiccator.

Titration of NTA

The NTA-containing compounds, Z-NTA, ε-amino-NTA, and F108-NTA were characterized by titrating the carboxylic acid groups with a standard NaOH solution to evaluate the synthesis. For comparison, commercially available NTA was also titrated. A 0.015 M sample solution for all of the NTA compounds was prepared. Titration was performed using a Radiometer Copenhagen Titration System (Denmark) with an ABU 80 Auto Burette and PHM84 Research pH Meter. A 10 ml sample solution was titrated by adding 0.1 M standard NaOH at 0.5 ml/min.

Surface Modification of Polystyrene Beads

Three different polystyrene (PS) surface modifications were used for our experiments: (1) PS beads coated with F108, (2) PS beads coated with F108-NTA and (3) PS beads coated with F108-NTA and charged with $Ni^{2+}$ ions. The adsorption of the F108 and F108-NTA was performed by incubating the PS beads (1% w/w) with the surfactant (4% w/w) in phosphate buffer (50 mM pH 7.8) overnight with constant end-over-end mixing at room temperature. The coated beads were then washed to remove unbound surfactant by centrifugation (Eppendoff centrifuge, 14 k rpm, 10 min). The washed beads were resuspended in D.I. water and stored at 4° C. The F108-NTA beads were charged with $Ni^{2+}$ by incubating in 50 mM $NiSO_4$ overnight with constant end-over-end mixing at room temperature. The $Ni^{2+}$ charged beads were washed and stored at 4° C.

Purification of FFL

The construction and purification of FFL was accomplished essentially using the methods described in Wang, C. Y.; Hitz, S.; Anrade, J. D.: Stewart, R. J.; *Anal. Biochem.*, 1997, 246, 133. In summary, a fragment containing the firefly luciferase gene was ligated into the pRSET expression vector encoding six histidine residues at the N-terminus. The FFL construct was expressed in *E coli* strain BL21(DE3) and the his-tagged FFL was purified from the cell lysate by immobilized metal affinity chromatography (IMAC).

FFL Adsorption

FFL was adsorbed onto PS beads by incubating FFL (65 μg in solution) with 150 μl 1% (w/w) PS beads in 800 μl 50 mM phosphate buffer (pH 7.8) overnight at 4° C. The amount adsorbed protein on the PS beads was determined by pelleting the beads by centrifugation, measuring the protein concentration in the supernatant, and subtracting supernatant concentration from the initial protein concentration. FFL concentrations were determined using a Bradford assay protein kit (Sigma) with bovine serum albumin as a standard. The PS bead concentration was determined by light scattering. A series of standard PS bead solutions (0.0005% (w/w) to 0.015% (w/w)) were prepared from a 10% (w/w) PS bead stock solution. A standard curve was created from of the optical density at 500 nm of the PS bead standard solutions.

The activity of FFL both in the supernatant and on the PS beads was determined using a luminometer (Turner Designs, model: TD-20/20). To measure the bioluminescent activity, 10 μl of FFL solution was added to a luminometer tube containing 100 μl of 0.02 mM luciferin and 0.02 mM $Mg^{2+}$ in 25 mM Gly—Gly buffer (pH 7.8). The reaction was initiated by the addition of ATP (140 μl, 0.01 mM in 25 mM Gly—Gly buffer) and the tube was immediately placed in the luminometer. Relative light intensity was integrated for three minutes.

Example I

Synthesis of F108-NTA

Figure 2:
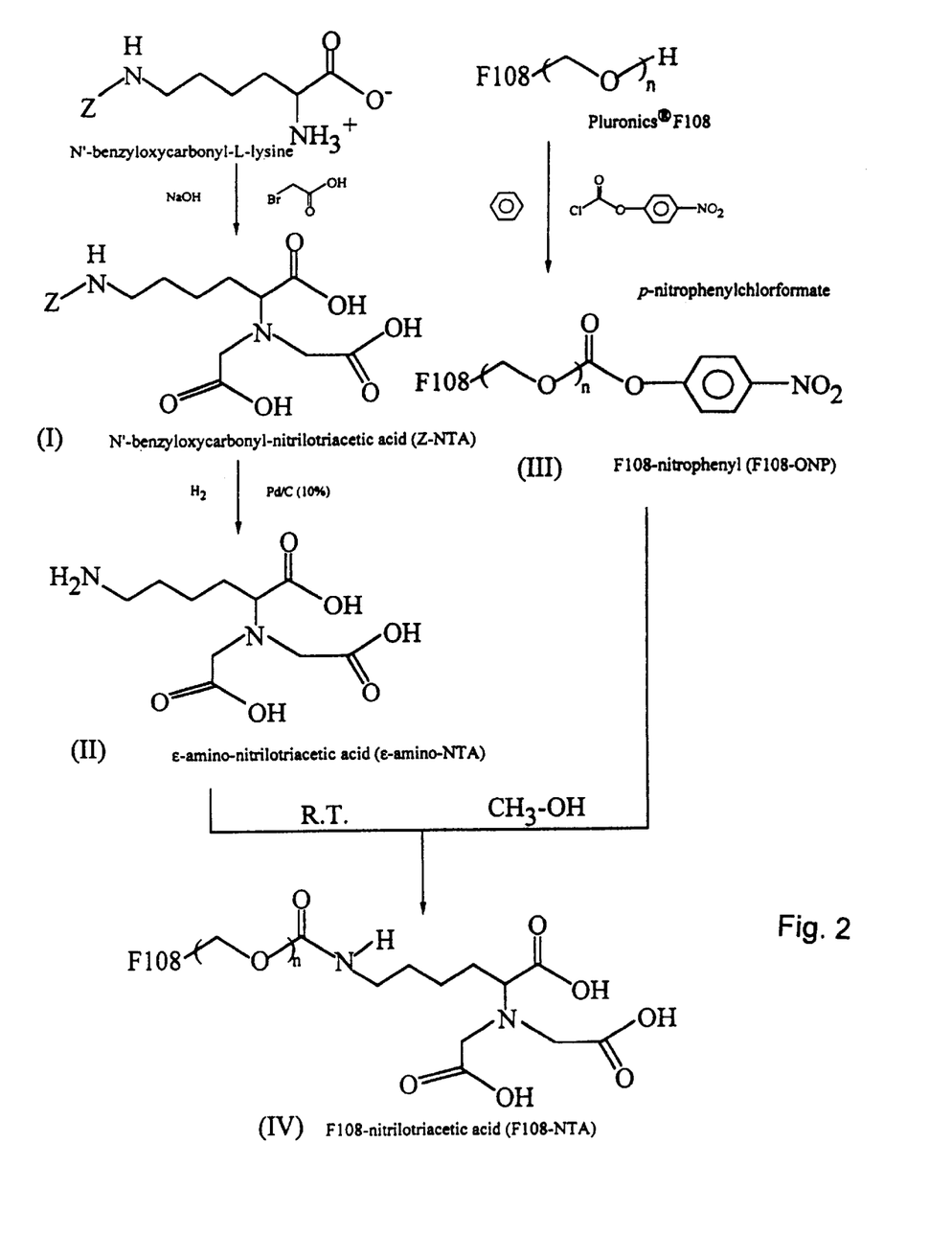
FIG. 2 is a flow sheet showing the chemical synthesis of P-surfactant F108-NTA.
Figure 3:
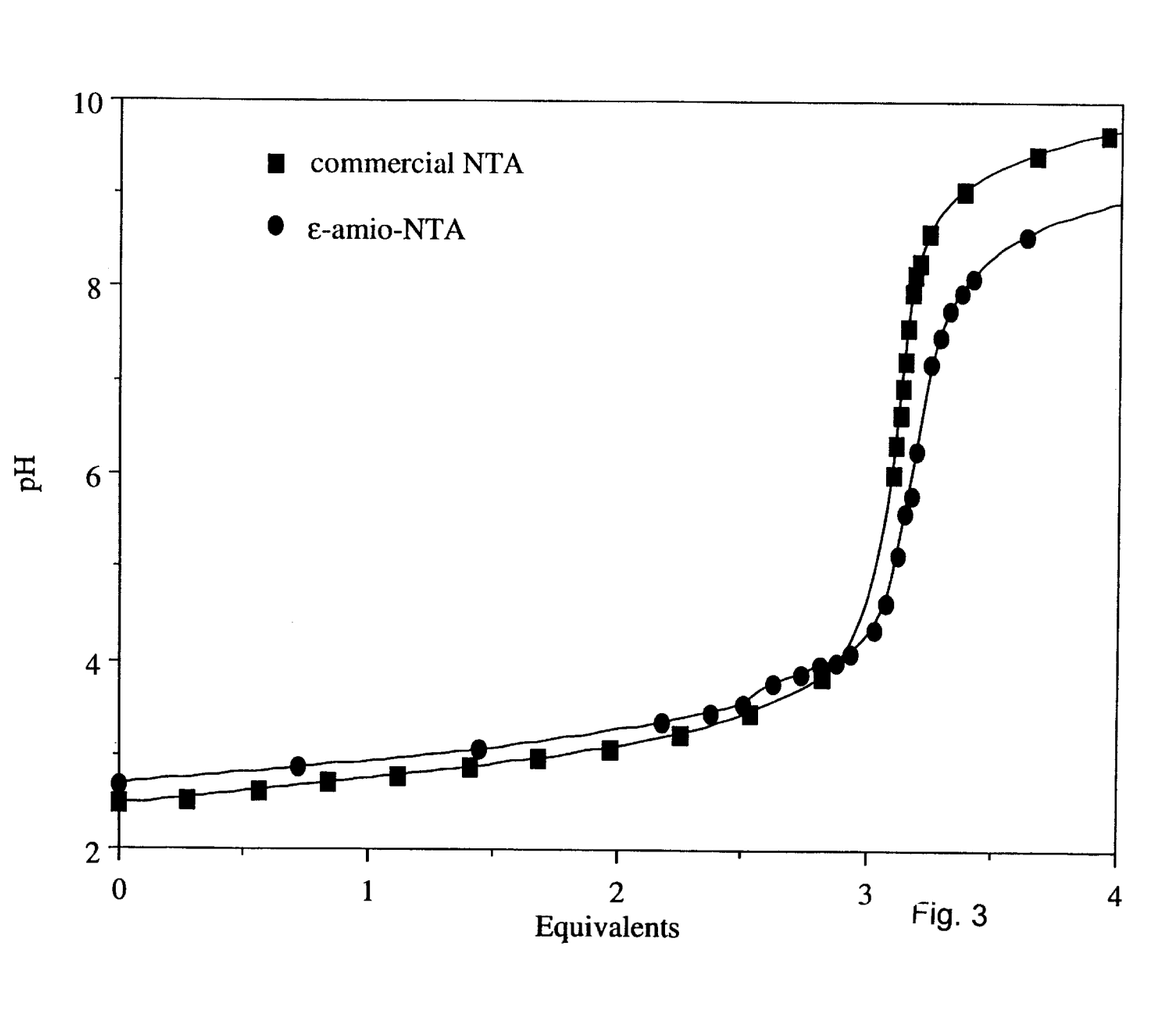
FIG. 3 is a graph showing titration analysis of ε-amino-NTA, using reagent grade NTA for comparison.
Figure 4:
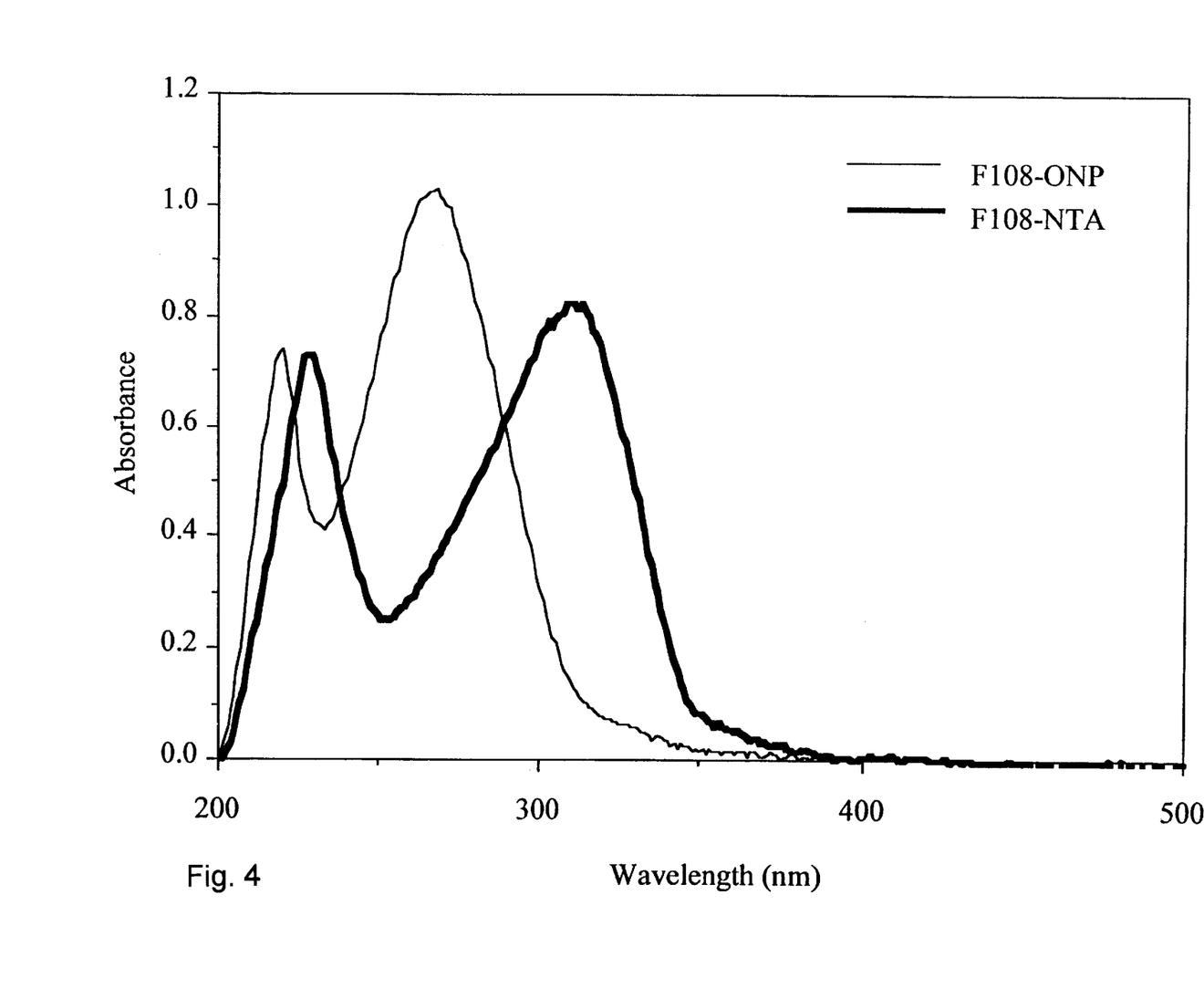
FIG. 4 is a graph showing the UV absorbance spectra of F108-ONP and F108-NTA.
Figure 5:
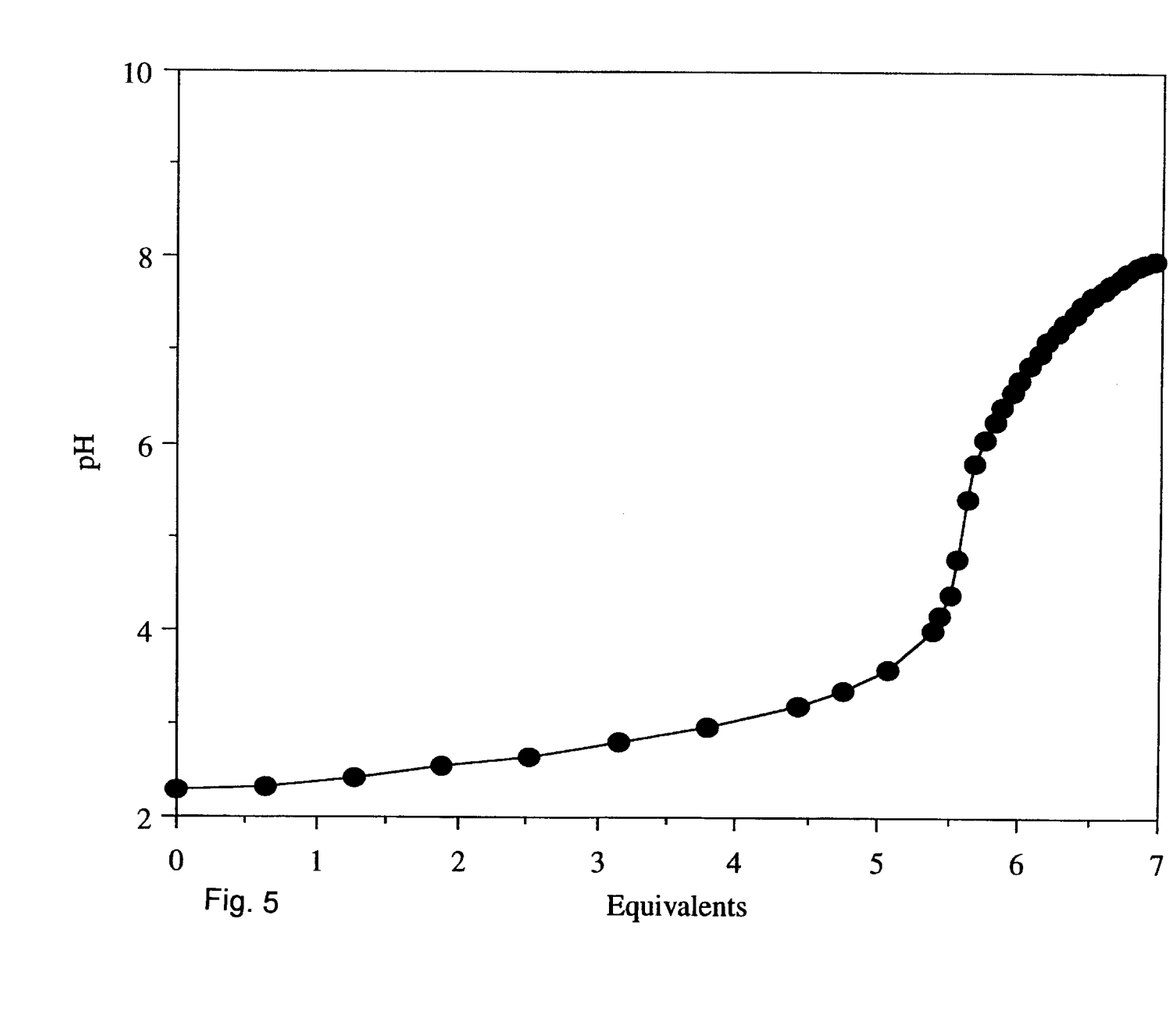
FIG. 5 is a graph showing the titration analysis of NTA-modified P-surfactant F108.

The synthesis of F108 with pendant metal-chelating NTA groups is outlined in FIG. 2. NTA with a primary amine group available for coupling (II) was synthesized following the procedure described in Hochuli, E. Dobeli, H.; Schacher, A. J. *Chrom*, 1987, 441, 177, by reacting N'-benzyloxycarbonyl-L-lysine with bromoacetate to form I. (Z in FIG. 2 is N-ε-benzyloxycarbonyl.) Titration of II (FIG. 3) indicated that it contained approximately 3 carboxylic acid groups per molecule, which was similar to commercial NTA. The melting point of II was 220–224° C., in agreement with literature values. To activate F108 for coupling to II, the terminal hydroxyl groups of the PEO chains of F108 were reacted with p-nitrophenyl chloroformate. The yield of III, assuming two available terminal hydroxyl groups per F108 molecule, was estimated to be 91% by hydrolyzing the purified reaction product in 0.1 M NaOH and measuring the concentration of free p-nitrophenyl spectrophotometrically. The reaction of II and III was monitored spectrophotometrically and allow to go to completion by following the shift in wavelength at the peak absorbance from 268 nm to 310 nm as p-nitrophenyl was released from III (FIG. 4). Titration of IV, after purification by ether precipitation and dialysis against water, indicated that the final product contained approximately 5.6 carboxylic acid groups per F108 molecule (FIG. 5), which suggests that if all F108 molecules had at least one NTA group, then 86% had two NTA groups. The inflection point of the titration curve was taken as the titration end point (5.6 equivalents).

Figure 2A:
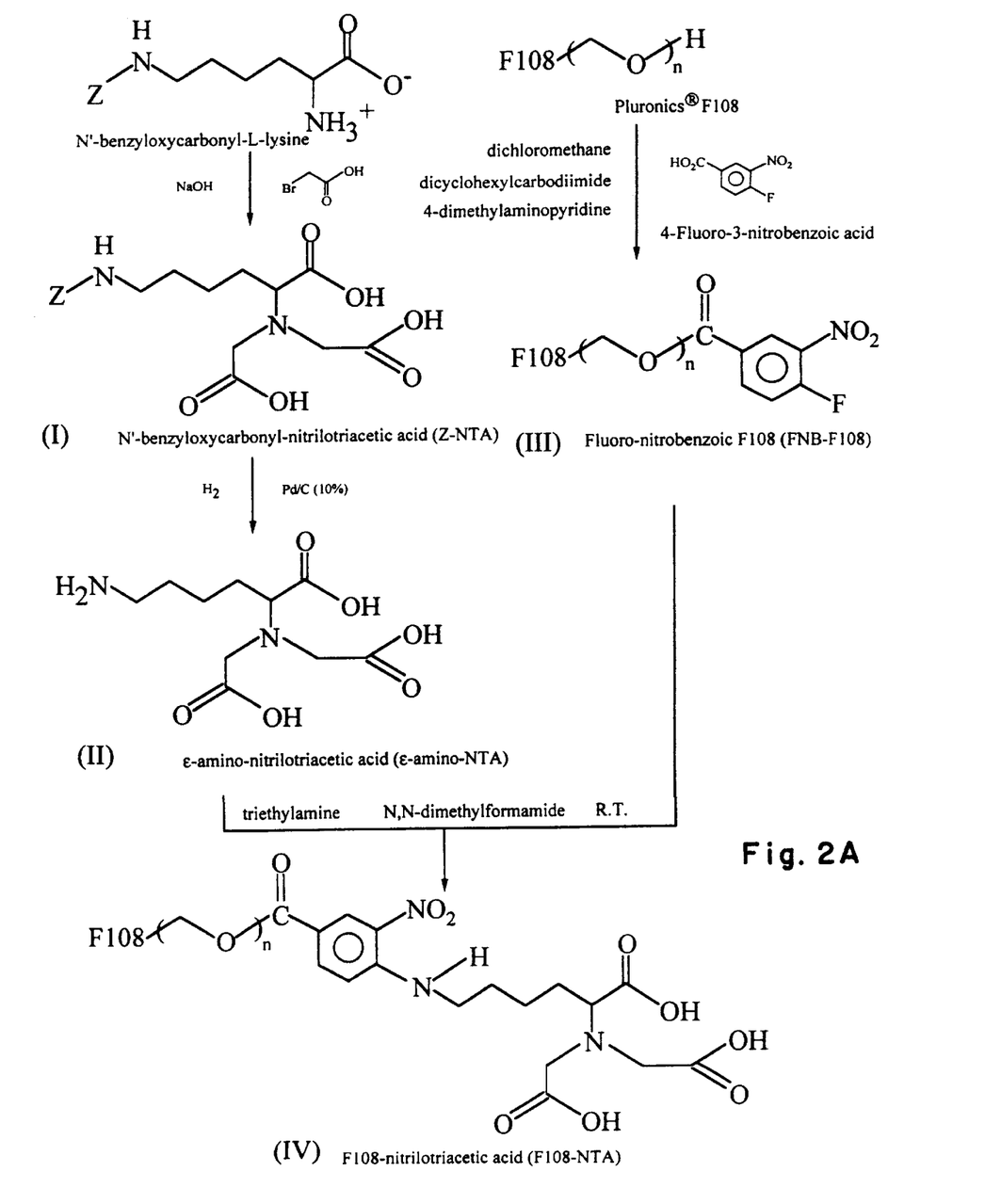
FIG. 2A is a flow sheet showing an alternate chemical synthesis of P-surfactant F108-NTA.

An alternate method for systhesis of F108/NTA is shown in FIG. 2A, wherein the P-surfactant is treated with 4-fluoro-3-nitrobenzoic acid to form fluoro-nitrobenzoic F108, which is in turn treated with N,N-dimethylformanide to form F108-NTA.

Example II

Firefly Luciferase Immobilization on Polystyrene Beads

Figure 6:
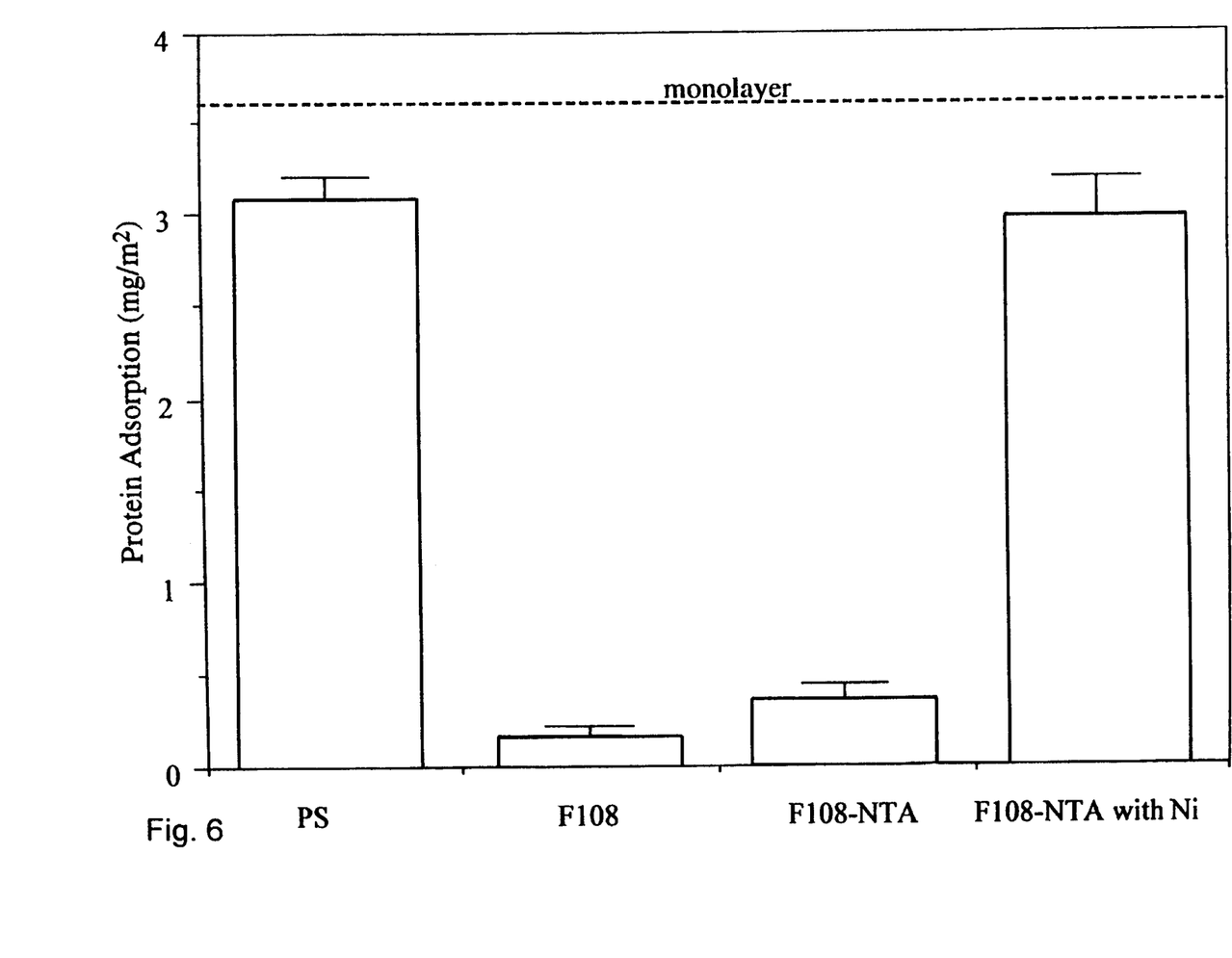
FIG. 6 is a bar graph comparing adsorption of firefly luciferace on non-treated and P-surfactant-treated polystyrene beads.

Protein immobilization by the chelating P-surfactant was evaluated using recombinant firefly luciferase (FFL). Adsorption of FFL onto polystyrene (PS) beads was estimated by incubating the beads with a known amount of FFL, then separating the beads by centrifugation, and determining the concentration of protein remaining in the supernatant. The bead surface area was estimated from the bead concentration, determined by light scattering, and the bead diameter. The adsorption of FFL to untreated and PS beads treated with chelating P-surfactants is shown in FIG. 6. The values represent an average of at least three protein adsorption measurements. The amounts of protein adsorption on untreated PS bead and PS beads treated with F108-NTA in the presence of $Ni^{2+}$ approached the theoretical monolayer. For comparison, the mass of a theoretical monolayer of FFL (dashed line) was calculated by approximating the adsorbed FFL as an unflattened sphere with a 6.5 nm radius, occupying a circular surface area with a 6.5 nm radius. As expected, adsorption of FFL by untreated PS beads (3.08 K 0.13 mg/m$^2$) approached the mass of a theoretical monolayer of FFL. On the other hand, PS beads treated with unmodified F108 adsorbed little FFL (0.15 K 0.07 mg/m$^2$), demonstrating that F108 effectively prevents non-specific adsorption of FFL to PS beads. Treatment of PS beads with the NTA-modified F108, in the absence of $Ni^{2+}$ ions, also inhibited FFL adsorption (0.35 K 0.09 mg/m$^2$). In the presence of $Ni^{2+}$ ions, the binding of FFL to the F108-NTA treated PS beads (2.99 K 0.20 mg/m$^2$) approached the theoretical monolayer. The finding that FFL bound to F108-NTA treated PS beads only in the presence of $Ni^{2+}$ demonstrated that binding occurred specifically through the histidine-tag of FFL to the chelated $Ni^{2+}$ ions.

Figure 7:
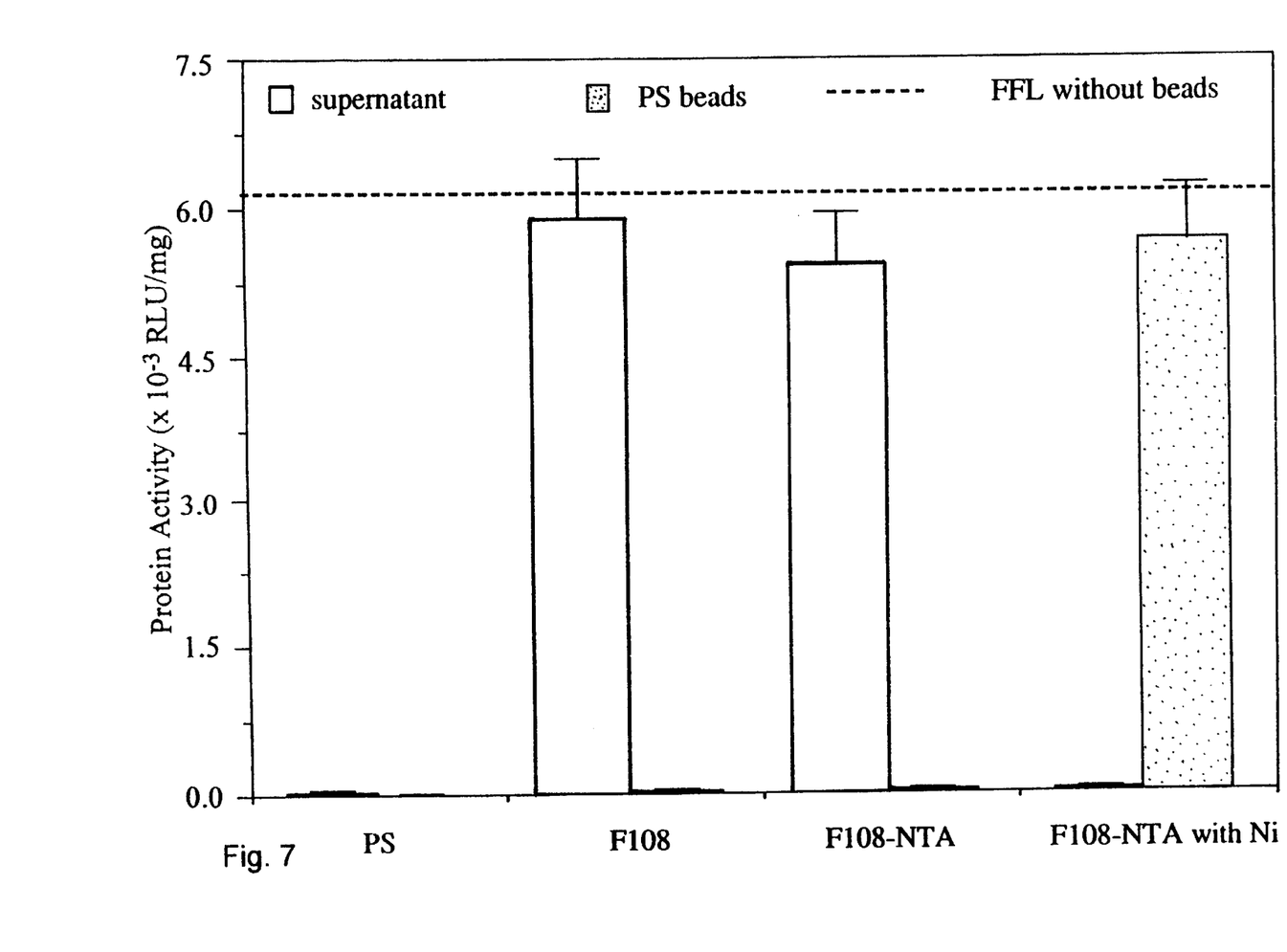
FIG. 7 is a bar graph comparing luciferase activity on non-treated and P-surfactant-treated beads.

An object of the invention was to develop a convenient, generally applicable, and activity preserving method of protein immobilization. By measuring the activity of the immobilized FFL, the preservation of activity can be demonstrated.. A sub-saturating concentration of FFL (65 μg/ml) was incubated with treated or untreated PS beads. Bound FFL was separated from unbound FFL by centrifugation, and the resulting supernatant and bead fractions were assayed for bioluminescence (FIG. 7). The dashed line in FIG. 7 represents the bioluminescent activity (6160 K 130 RLU) of an equivalent concentration of FFL (65 μg/ml) in the absence of any beads. The values represent the average of at least three bioluminescence measurements. FFL immobilized on F108-NTA in the presence of $Ni^{2+}$ retained approximately 93% of its activity.

Following incubation with untreated PS beads, which bind FFL non-specifically, there was no bioluminescence in either the supernatant or the resuspended bead pellet; the FFL had been quantitatively adsorbed and inactivated by the untreated PS beads. Following incubation with F108-treated PS beads virtually all of the bioluminescence (5840 K 65 RLU) remained in the supernatant. The small difference between the F108 bead supernatant and the control solution may be due to light scattering by the beads. After incubation with F108-NTA treated beads, in the absence of $Ni^{2+}$, the bioluminescence remained mostly in the supernatant (5350 K 62 RLU), although the activity was slightly less than that found after incubation with beads treated with unmodified F108, which was consistent with the bulk binding data (FIG. 6). After incubation with F108-NTA treated beads, in the presence of $Ni^{2+}$, nearly all of the bioluminescence (5650 K 57 RLU) was found in the resuspended bead pellet and virtually no activity remained in the supernatant, demonstrating that FFL was specifically immobilized with high specific activity.

Figure 8:
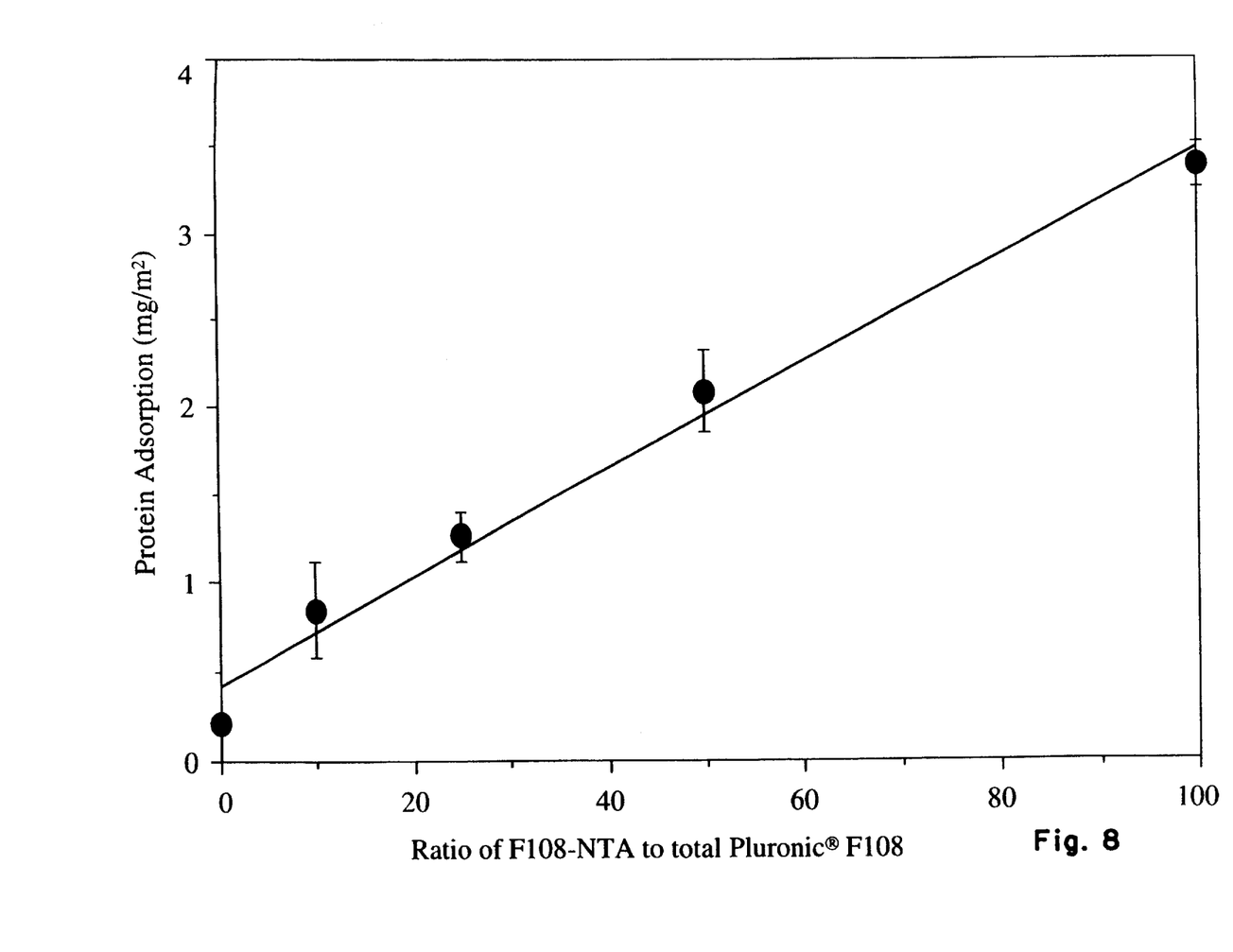
FIG. 8 is a graph showing adsorption of firefly luciferace onto PS beads treated with ratios of F108-NTA to P-surfactant F108 of 0, 0.1, 0.25, 0.5, and 1.0

The results show that activation of the terminal hydroxyl groups of P-surfactant F108 with p-nitrophenyl chloroformate, followed by reaction with ε-amino-NTA, resulted in the efficient synthesis of P-surfactant F108 with pendant metal-chelating groups. From titration data (FIG. 5), at least 86% of the final F108 molecules contained two NTA groups. The resulting F108-NTA reagent is soluble in water or organic solvents, and can be stored indefinitely in solution, or as a powder. To prepare a stable, activity preserving surface for specifically immobilizing histidine-tagged proteins, the reagent is simply adsorbed to hydrophobic surfaces, like polystyrene beads or plasticware. Furthermore, the surface density of chelating groups, and thereby the surface density of protein, can be controlled by mixing F108-NTA with underivatized F108 before adsorption to the surface. (See FIG. 8) For many applications, the simplicity of the P-surfactant-based chemistry and surface modification provides a practical advantage over other methods of protein immobilization.

F108-NTA was evaluated as a protein immobilization reagent using recombinant firefly luciferase, which was an appropriate test protein for several reasons. First, the activity of the immobilized luciferase-ATP-dependent bioluminescence was conveniently and accurately determined by luminometry. Second, the convenience, specificity, and sensitivity of the FFL bioluminescence reaction has generated considerable interest in FFL-based biosensors. As part of FFL-based biosensor development, an effective method is needed to immobilize FFL with high specific activity. Third, FFL is known to be sensitive to conventional immobilization methods; both chemical coupling and physical adsorption of luciferase to surfaces have been ineffective, generally resulting in enzyme inactivation and denaturation. FFL was adsorbed and completely inactivated on the surface of untreated polystyrene beads. On the other hand, when immobilized in the presence of $Ni^{2+}$ on F108-NTA treated polystyrene beads, FFL retained about 93% of its bioluminescence activity (See FIG. 7). The small difference between luciferase activity in solution and activity immobilized on the beads could be due to light scattering by the beads rather than to protein inactivation as a result of immobilization. These results demonstrated that the F108-NTA provided an effective method for immobilizing active FFL, which may be useful for developing FFL-based biosensors.

The above example illustrates that metal-chelating P-surfactants provide a convenient method to specifically immobilize histidine-tagged firefly luciferase on submicron polystyrene beads with high specific activity. The P-surfactant-based method is convenient, chemically robust, and is likely to be generally applicable to many hydrophobic surfaces, to which one wishes to attach proteins and generally applicable to recombinant proteins, some non-recombinant proteins, and cells expressing recombinant proteins on their surface. Since proteins are immobilized through a consistent linkage, with a defined orientation, and with little loss of activity, the method may be particularly useful for single-molecule micromechanical experiments using scanned tip microscopes or optical tweezers.

Example III
Metal-Chelating P-surfactant for ELISA (Enzyme Linked Immunosorbent Assay)

F108-NTA is made as in Example I and adsorbed into wells of microtiter plates. The coated plates are then incubated in solution containing $Ni^{2+}$ to form a coating of a metal-ion complex. Protein A that has histidine tags is then bound to the metal-ions, and the Protein A is thereafter bound to an antibody. Alternately, a histidine-tagged recombinant antibody is bound to the metal ion, or an antibody with a chemically added chelating group is bound to the metal ions. This method can be modified as required for any receptor/ligand binding for analytical or diagnostic purposes.

Metal-Chelating P-surfactant for Mechanical Measurements

A research area that will benefit from a standardized immobilization procedure is for mechanical measurements of single protein molecules using optical tweezer-based instruments, or scanned tip microscopes. So far, these experiments have relied on non-specific adsorption to couple the protein of interest to the probe surface, in some cases the protein was directly adsorbed on the probe surface, while in other cases a protein that specifically recognizes the protein of interest is non-specifically adsorbed to the probe surface.

The advantage of the chelating P-surfactants for single-molecule, micromechanical experiments is that they provide a well-defined and consistent linkage to the probe surface. The P-surfactant foundation is consistently oriented on the hydrophobic surface and the protein binds specifically through a terminal histidine-tag. The result is that the mechanical properties of the linkage will be consistent for each protein molecule in an experiment, and consistent between various recombinant forms of the protein. Since the attachment is chemically defined, it is believed possible, if necessary, to adjust the linkage compliance between the protein and probe by using a P-surfactant with shorter or longer PEO blocks. The chelating P-surfactant should be useful for proteins being investigated at the single molecule level.

Metal-Chelating P-surfactant for Immobilization of Cells on a Substrate

The present invention is also useful in applications where cells are to be immobilized upon a surface for cell growth, or for bioreactor, or tissue engineering.

While this invention has been described with reference to certain specific embodiments and examples, it will be recognized by those skilled in the art that many variations are possible without departing from the scope and spirit of this invention, and that the invention, as described by the claims, is intended to cover all changes and modifications of the invention which do not depart from the spirit of the invention. For example, the method is believed to be generally applicable to most histidine-tagged proteins and many hydrophobic interfaces.

What is claimed is:

1. A compound comprising at least one PEO block having a first end and a second end, the PEO block attached at its first end to at least one PPO block, with at least one of the PEO blocks having a metal-chelating end group (R) attached to its second end, with any remaining PEO blocks without R having an unmodified hydroxyl group at the second end.

2. A compound as in claim 1 wherein there are between 1 and 6 PEO blocks attached to between 1 and 3 PPO blocks.

3. A compound as in claim 1 wherein the number of —($C_3H_6$)— units in the PPO blocks is the same or different and is at least 25, and the number of —($C_2H_4$)— units in the PEO blocks is the same or different and is at least 50.

4. A compound as in claim 1 wherein R is selected from the group comprising NTA IDA, BCA, and TED.

5. A compound as in claim 1 additionally comprising a metal-ion bound to the metal-chelating R group.

6. A compound as in claim 5 wherein the metal-ion is selected from the group consisting of transition-metal ions, lanthanide-metal ions, and actinide-metal ions.

7. A compound as in claim 6 wherein the metal-ion is selected from the group consisting of ions of Ni, Cu, Zn, and Gd.

8. A complex comprising a compound comprising at least one PEO block having a first end and a second end, the PEO block attached at its first end to at least one PPO block, with at least one of the PEO blocks having a metal-chelating end group (R) attached to its second end, with any remaining PEO blocks without R having an unmodified hydroxyl group at the second end, the protein comprising a metal affinity tag with the compound bound to the protein by the metal-affinity tag on the protein complexed with a metal-ion.

9. A complex as in claim 8 wherein the metal-affinity tag is a histidine sequence.

10. A complex as in claim 9 wherein the histidine tag comprises a sequence of between 3 and 6 histidines.

11. A compound as in claim 1 wherein the compound is adsorbed upon a hydrophobic interface.

12. A compound as in claim 11 wherein the interface is a solid/liquid interface.

13. A compound as in claim 11 wherein the interface is a liquid/liquid interface.

14. A compound as in claim 11 wherein the compound is in a micelle.

15. A compound as in claim 11 wherein the compound is in a gel.

16. A compound as in claim 11 wherein the compound is in an emulsion.

17. A composition for the immobilization of proteins upon an interface comprising a hydrophobic interface with a metal-chelating surfactant adsorbed upon the hydrophobic interface, the metal-chelating surfactant comprising at least one PEO block having a first end and a second end, the PEO block attached at its first end to at least one PPO block, with at least one of the PEO block having an organic metal-chelating end group (R) attached to its second end, with any remaining PEO blocks without R having an unmodified hydroxyl group at the second end.

18. A composition as in claim 14 wherein there are between 1 and 6 PEO blocks attached to between 1 and 3 PPO blocks.

19. A composition as in claim 14 wherein the number of —($C_3H_6$)— units in the PPO blocks is the same or different and is at least 25, and the number of —($C_2H_4$)— units in the PEO blocks is the same or different and is at least 50.

20. A composition as in claim 14 wherein R is selected from the group comprising NTA, IDA, BCA, and TED.

21. A composition as in claim 14 additionally comprising a metal-ion bound to the metal-chelating R group.

22. A composition as in claim 21 wherein the metal-ion is selected from the group consisting of transition-metal ions, lanthanide-metal ions, and actinide-metal ions.

23. A composition as in claim 22 wherein the metal-ion is selected from the group consisting of ions of Ni, Cu, Zn, and Gd.

24. A composition as in claim 21 wherein the compound is bound to a protein by a metal-affinity tag on the protein complexed with the metal-ion.

25. A composition as in claim 24 wherein the metal-affinity tag is a histidine sequence.

26. A composition as in claim 14 wherein the interface is a solid/liquid interface.

27. A composition as in claim 14 wherein the interface is a liquid/liquid interface.

28. A composition as in claim 14 wherein the compound is in a micelle.

29. A composition as in claim 14 wherein the compound is in a gel.

30. A composition as in claim 14 wherein the compound is in an emulsion.

31. A composition as in claim 25 wherein the histidine sequence comprises a sequence of between 3 and 6 histidines.

32. A method for immobilizing a protein upon a hydrophobic surface comprising:

(1) adsorbing a modified surfactant having metal-chelating end groups upon a hydrophobic surface to form a layer coating of the modified surfactant on the surface, the modified surfactant having at least one PEO block having a first end and a second end, the PEO block attached at its first end to at least one PPO block, with at least one of the PEO block having an organic metal-chelating end group (R) attached to its second end, with any remaining PEO blocks without R having an unmodified hydroxyl group at the second end;

(2) charging the modified surfactant coating by contacting the coating surface with an aqueous solution containing a metal ion to form a chelated metal-ion complex of the metal-ion and the modified surfactant coating adsorbed upon the hydrophobic surface;

(3) contacting the charged coating with an aqueous solution containing a protein having a metal-affinity tag to link the metal-affinity tag with the chelated metal ion.

* * * * *